United States Patent
Johnson et al.

(10) Patent No.: US 9,357,946 B2
(45) Date of Patent: Jun. 7, 2016

(54) BREATH CONDENSATE SAMPLER AND DETECTOR AND BREATH/BREATH CONDENSATE SAMPLER AND DETECTOR

(75) Inventors: Bradley N. Johnson, Berkeley, CA (US); Kanchan Joshi, Emeryville, CA (US); Ying-Lan Chang, Cupertino, CA (US); Ray Radtkey, Oakland, CA (US)

(73) Assignee: Nanomix, Inc., Emeryville, CA (US)

( * ) Notice: Subject to any disclaimer, the term of this patent is extended or adjusted under 35 U.S.C. 154(b) by 718 days.

(21) Appl. No.: 12/761,290

(22) Filed: Apr. 15, 2010

(65) Prior Publication Data

US 2010/0268106 A1 Oct. 21, 2010

Related U.S. Application Data

(60) Provisional application No. 61/169,655, filed on Apr. 15, 2009.

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/0803* (2013.01); *A61B 5/14539* (2013.01); *B82Y 30/00* (2013.01); *G01N 33/497* (2013.01); *G01N 2001/2282* (2013.01)

(58) Field of Classification Search
USPC ..................... 600/529–543; 435/287.2–287.3
See application file for complete search history.

(56) References Cited

U.S. PATENT DOCUMENTS 5,502,533 A * 3/1996 Biegler .......................... 396/565
8,366,630 B2 * 2/2013 Haick et al. ................... 600/532
(Continued)

FOREIGN PATENT DOCUMENTS

CN 101238980 A 3/2008
JP 2000-507462 6/2000
(Continued)

OTHER PUBLICATIONS

PCT Notification of Transmittal of the International Search Report and the Written Opinion of the International Searching Authority, or the Declaration, mailed Jun. 16, 2010, Application No. PCT/US 2010/031307.
(Continued)

*Primary Examiner* — Navin Natnithithadha
*Assistant Examiner* — Eric Messersmith
(74) *Attorney, Agent, or Firm* — Weaver Austin Villeneuve & Sampson LLP

(57) ABSTRACT

The present invention provides a direct sampler and detector for analytes found in exhaled breath condensate. Analytes in the breath condensate are detected instantaneously as they condense prior to reaching the sensor surface or condense directly on the sensor surface. Because the analysis or assay is performed immediately after patient exhalation, analyte stability is significantly improved providing accurate, reliable, consistent, and clinically applicable results. In certain embodiments, combined breath condensate/breath samplers and detectors are provided, enabling multiplexed analysis of condensed and vapor-phase analytes provided in a single sampling session. Breath is collected and directed to one or more subsystems. Within each subsystem, the breath portion is either condensed or prevented from condensing. The technique also allows real-time continuous monitoring, thus allowing immediate feedback to both medical professionals and additional hardware such as ventilators, anesthesia machines, drug infusion systems and cardiac pacemakers.

36 Claims, 11 Drawing Sheets

(51) Int. Cl.
*A61B 5/145* (2006.01)
*B82Y 30/00* (2011.01)
*G01N 33/497* (2006.01)
*G01N 1/22* (2006.01)

(56) References Cited

U.S. PATENT DOCUMENTS

| | | | | |
|---|---|---|---|---|
| 8,481,324 | B2* | 7/2013 | Haick et al. | 436/63 |
| 8,557,518 | B2* | 10/2013 | Jovanovich et al. | 435/6.1 |
| 2003/0065275 | A1* | 4/2003 | Mault et al. | 600/531 |
| 2004/0162500 | A1* | 8/2004 | Kline | 600/532 |
| 2004/0210151 | A1* | 10/2004 | Tsukashima et al. | 600/532 |
| 2006/0040318 | A1* | 2/2006 | Melker et al. | 435/7.1 |
| 2007/0048180 | A1* | 3/2007 | Gabriel et al. | 422/57 |
| 2007/0167853 | A1* | 7/2007 | Melker et al. | 600/532 |
| 2007/0173731 | A1* | 7/2007 | Meka et al. | 600/543 |
| 2008/0064113 | A1* | 3/2008 | Goix et al. | 436/86 |
| 2008/0183094 | A1* | 7/2008 | Schonfuss et al. | 600/532 |
| 2009/0275852 | A1* | 11/2009 | Oki et al. | 600/532 |

FOREIGN PATENT DOCUMENTS

| | | |
|---|---|---|
| JP | 2007-505314 | 3/2007 |
| JP | 2008-538816 A | 11/2008 |
| WO | 97-35519 | 10/1997 |
| WO | 2005-025417 | 3/2005 |
| WO | 2006-114335 | 11/2006 |

OTHER PUBLICATIONS

Japanese Office Action dated Aug. 13, 2013, issued in Application No. 2012-505940.
Chinese Office Action dated Dec. 2, 2013, issued in Application No. 201080027418.1.
European Supplemental Search Report dated Apr. 7, 2014, issued in Application No. 10765214.1.
Chinese Office Action dated Sep. 3, 2014, issued in Application No. 201080027418.1.
Japanese Office Action dated Mar. 11, 2014, issued in Application No. 2012-505940.
Japanese Office Action dated Dec. 2, 2014, issued in Application No. 2012-505940.
Japanese Office Action dated Jul. 7, 2015, issued in Application No. JP2012-505940.
Chinese Office Action dated Apr. 28, 2015, issued in Application No. 201080027418.1.

* cited by examiner

BREATH CONDENSATE SAMPLER AND DETECTOR AND BREATH/BREATH CONDENSATE SAMPLER AND DETECTOR

CROSS-REFERENCE TO RELATED APPLICATION

This application claims the benefit pursuant to 35 USC. §119(e) of the following US Provisional Application, which is incorporated by reference in its entirety: U.S. Provisional Patent Application No. 61/169,655, filed Apr. 15, 2009.

BACKGROUND

Exhaled breath condensate (EBC) contains various constituents including small molecules, proteins and DNA. Measuring the presence or quantity of these constituents in a patient's exhaled breath condensate can provide diagnostic and other information including pH, the presence of various proteins including anti-inflammatory or pro-inflammatory cytokines, etc. To date, however, breath condensate samplers require a patient to exhale breath into a sampling tube over a fairly long period of time, e.g., ten minutes, to collect the necessary amount of sample. This is time-consuming as well as physically difficult for patients. The tube is then sent off for separate analysis of the collected sample at a laboratory.

SUMMARY

The present invention provides a direct sampler and detector for analytes found in exhaled breath condensate. Analytes in the breath condensate are detected instantaneously as they condense prior to reaching the sensor surface or condense directly on the sensor surface. Because the analysis or assay is performed immediately after patient exhalation, analyte stability is significantly improved providing accurate, reliable, consistent, and clinically applicable results. In certain embodiments, combined breath condensate/breath samplers and detectors are provided, enabling multiplexed analysis of condensed and vapor-phase analytes provided in a single sampling session. Breath is collected and directed to one or more subsystems. Within each subsystem, the breath portion is either condensed or prevented from condensing. The technique also allows real-time continuous monitoring, thus allowing immediate feedback to both medical professionals and additional hardware such as ventilators, anesthesia machines, drug infusion systems and cardiac pacemakers.

One aspect of the invention is a novel sampling scheme for breath. The sampling schemes described herein permit real-time or near real time measurement by condensing the condensate directly on the sensor surface or providing microfluidic and/or capillary flow paths that deliver condensate to the sensor after condensation. In certain embodiments, the device sensors incorporate nanostructured elements, e.g., carbon nanotubes. These sensors enable faster sensing with a relatively small amount of analyte. Reduced sample volume is critical for short sampling times, reduced power requirements for cooling and multiplexed testing.

In certain embodiments, combined breath condensate/breath sampler and detectors are provided. Also provided are sampling protocols in which a patient exhales one or more times into a single tube or other input port, with the device configured to receive a gaseous sample and a condensate sample, either simultaneously or consecutively, detecting one or more analytes in each sample. Systems described herein include these devices and further include data analysis components to receive breath condensate derived data and (gaseous) breath-derived data and produce combined metrics using both the breath condensate data and the breath data. In certain embodiments, for example, the sampling schemes enable real-time measurement of a patient's ratio of cysteinyl leukotriene (CysLT) level to eosinophilic airway inflammation.

DETAILED DESCRIPTION

Figure 1:
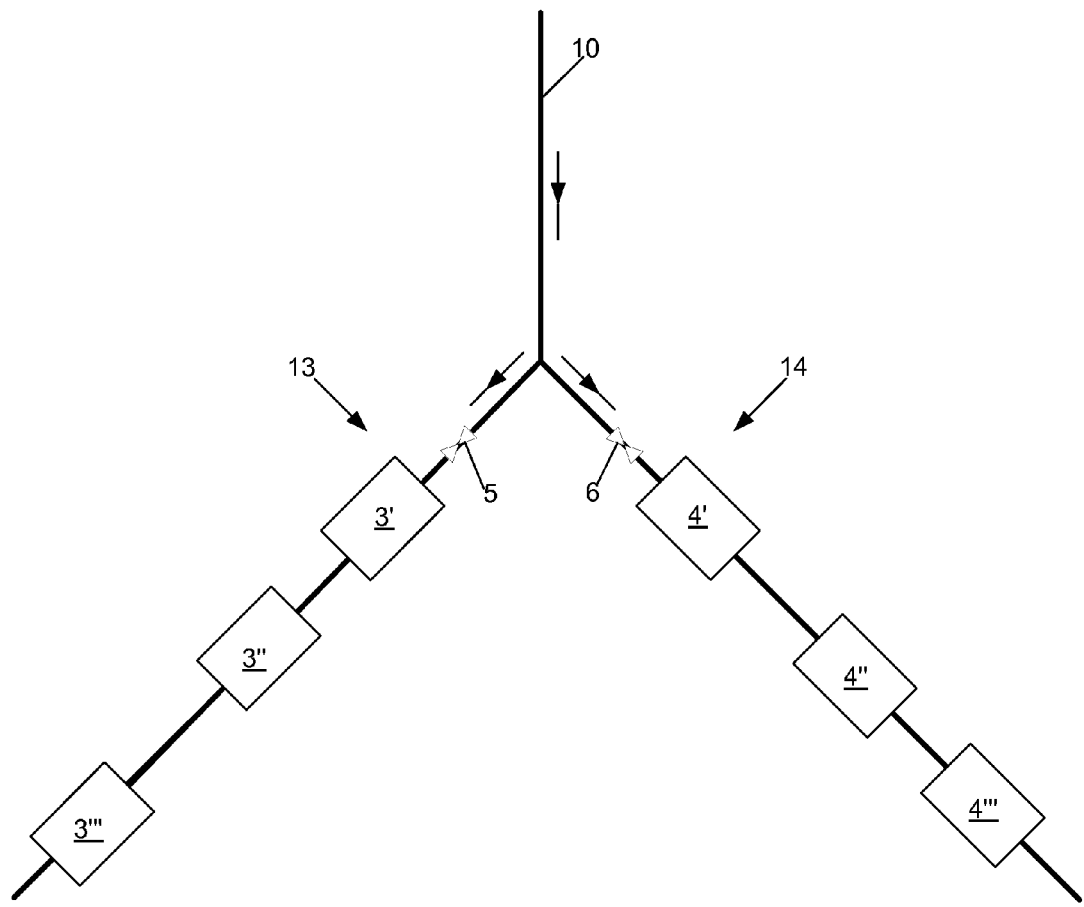
FIGS. 1-4D present schematic diagrams of flow path configurations for combined breath condensate and breath samplers and detectors according to certain embodiments.

In the following description, numerous details are set forth in order to provide a thorough understanding of the present invention. The present invention may be practiced without some or all of these details. In other instances, well known process operations have not been described in detail to not unnecessarily obscure the present invention. While the invention will be described in conjunction with the specific embodiments, it will be understood that it is not intended to limit the invention to the embodiments. References herein to physical vapor deposition, chemical vapor deposition, and atomic layer deposition are intended to cover many variants of these processes, including processes that are assisted with plasma, vacuum or low pressure processes, atmospheric pressure processes, etc.

Introduction

Exhaled breath condensate (EBC) contains various constituents including small molecules, proteins and DNA. Measuring the presence or quantity of these constituents in a patient's exhaled breath condensate can provide diagnostic and other information including pH, the presence of various proteins including anti-inflammatory or pro-inflammatory cytokines, etc. To date, however, breath condensate samplers require a patient to exhale breath into a sampling tube over a fairly long period of time, e.g., ten minutes, to collect the necessary amount of sample. This is time-consuming as well as physically difficult for patients. The tube is then sent off for separate analysis of the collected sample at a laboratory.

The present invention provides a direct sampler and detector for analytes found in exhaled breath condensate. Analytes in the breath condensate are detected instantaneously as they condense prior to reaching the sensor surface or condense directly on the sensor surface. Because the analysis or assay is performed immediately after patient exhalation, analyte stability is significantly improved providing accurate, reliable, consistent, and clinically applicable results. In certain embodiments, combined breath condensate/breath samplers and detectors are provided, enabling multiplexed analysis of condensed and vapor-phase analytes provided in a single sampling session. Breath is collected and directed to one or more subsystems. Within each subsystem, the breath portion is either condensed or prevented from condensing. The technique also allows real-time continuous monitoring, thus allowing mediate feedback to both medical professionals and additional hardware such as ventilators, anesthesia machines, drug infusion systems and cardiac pacemakers.

The sampling schemes described herein permit real-time or near real time measurement by condensing the condensate directly on the sensor surface or providing flow paths that deliver condensate to the sensor after condensation. In certain embodiments, the device sensors incorporate nanostructured elements, e.g., carbon nanotubes. These sensors enable faster sensing with a relatively small amount of analyte. Reduced sample volume is critical for short sampling times, reduced power requirements for cooling and multiplexed testing.

In certain embodiments, combined breath condensate/breath sampler and detectors are provided. Also provided are sampling protocols in which a patient exhales one or more times into a single tube or other input port, with the device configured to receive a gaseous sample and a condensate sample, either simultaneously or consecutively, detecting one or more analytes in each sample. Systems described herein include these devices and further include data analysis components to receive breath condensate derived data and (gaseous) breath-derived data and produce combined metrics using both the breath condensate data and the breath data. In certain embodiments, for example, the sampling schemes enable real-time measurement of a patient's ratio of cysteinyl leukotriene (CysLT) level to eosinophilic airway inflammation. See, U.S. Patent Publication No. 2009-0233963, titled "Methods To Determine Susceptibility To Treatment With Leukotriene Modifiers," incorporated by reference herein.

In certain embodiments, small, portable sampler and detector units are provided for uses in clinical settings. After a patient exhales into a conduit or input port or channel that is connected to or part of the portable unit, the breath sample passes through any number of breath condensation and/or breath gas sub-systems. The sub-systems may include sample conditioning sub-systems, fluid property measurement sub-systems, and detection sub-systems. A particular sub-system may be one or multiple types of these sub-systems. For example, a single sub-system may both condition the sample and detect analytes within the sample. The breath sample may pass through these sub-systems serially or in parallel (i.e., with the sample divided into sub-samples). Within the sub-systems, the breath gas and/or breath condensate may encounter features that condition the sample fluid, perform measurements of the fluid properties, and assay for the existence or quantity of known and unknown constituents.

Sub-systems that condition the sample fluid (liquid or gas) include sub-systems that condense or prevent the sample from condensing as appropriate. Sub-systems that perform measurements of the fluid properties include sub-systems to perform measurements of the temperature, relative humidity (RH), viscosity, conductivity and other fluid properties of the sample. In certain embodiments, a sub-system includes components to condition the sample and measure sample properties. For example, in a sample condenser, relative humidity and/or temperature measurements may be made. In certain embodiments, a sub-system is configured to assay the existence and/or quantity of particular predetermined constituents (e.g. protons, metabolites, nucleic acids, proteins, enzymes, ions, salts, etc) using appropriate methods. These methods include, though are not limited to, conductivity, ion-sensitive field-effect transistor (ISFET), enzyme-linked immunosorbent assays (ELISA) including optical ELISA and amperometric ELISA, end-point polymerase chain reaction (PCR) and real-time PCR. In certain embodiments, a sub-system is configured to assay the fluid for the existence and/or quantity of a priori unknown constituents (e.g. protons, metabolites, nucleic acids, proteins, enzymes, ions, salts, etc) using appropriate methods. These methods include, though are not limited to mass-spectroscopy and NMR. The assay methods are followed in certain embodiments by signal analysis methods to identify the components within the fluid. In certain embodiments, portable units include signal processing components including software and/or hardware. In certain embodiments, collected data are sent to other components (e.g., in lab or clinic computers) for processing.

In certain embodiments, after passing through the various sub-systems in the flow configuration pathway(s), the fluid or fluids can pass through the system and then collect in appropriate receiving containers (e.g. microfuge tubes, microtiter plates, Tedlar bags, Mylar bags, glass containers, capillaries, etc) to allow for off-line analysis using appropriate sample analysis techniques.

Figure 2:
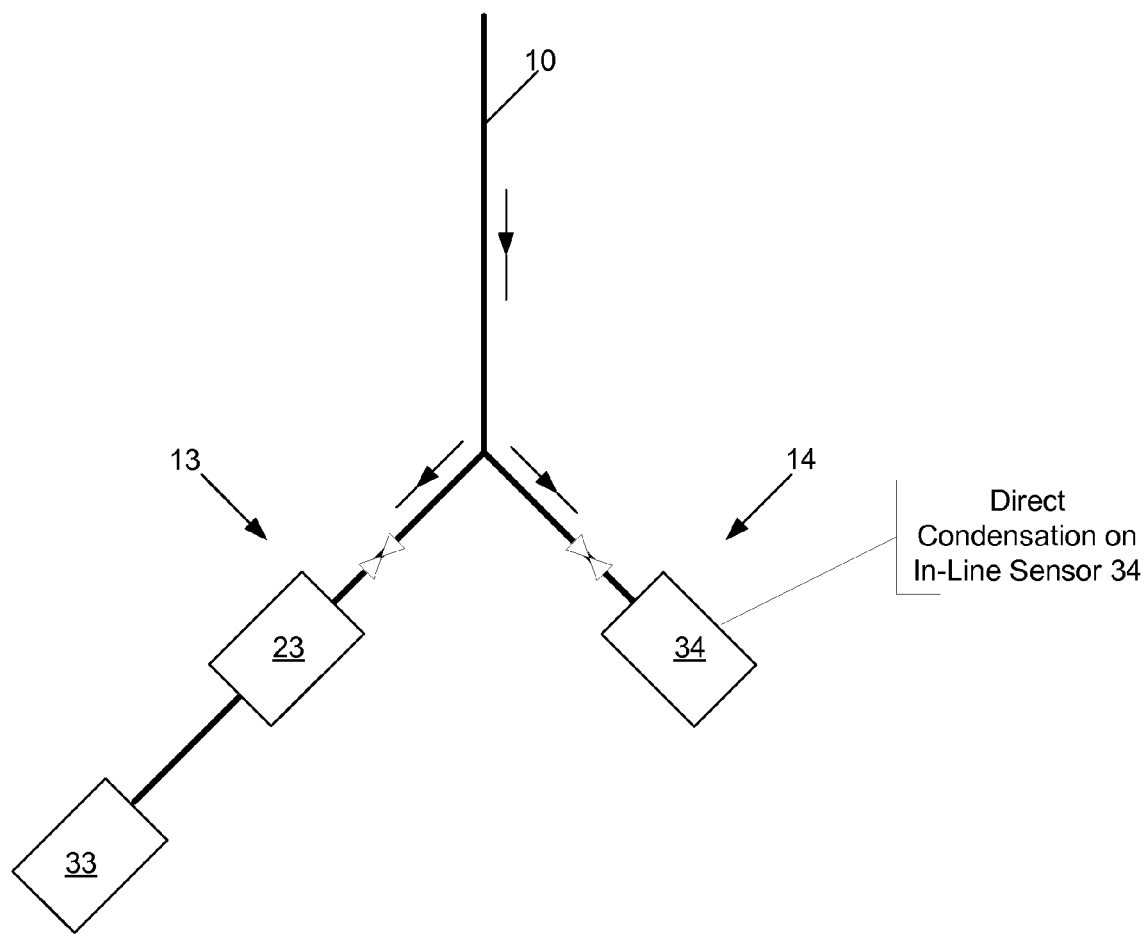

FIGS. 1-3 are schematic diagrams of example flow path configurations for a combined breath condensate/breath sampler and detector unit. While combined breath condensate/breath units are described, in other embodiments breath condensate units are provided. One of skill in the art will understand how to derive the flow path configurations for such units may be derived from these figures by considering only the breath condensate pathways.

First in FIG. 1, a flow path configuration including various breath and breath condensate sub-systems is depicted. Input channel 10 receives exhaled breath from a patient, either directly, or after the breath has passed through one or more input ports or other input channels. Input channel 10 bifurcates into a breath sensing channel 13 and a breath condensate channel 14. In certain embodiments, flow into each of channels 13 and 14 is controlled by a valve 5 and 6, respectively. According to various embodiments, the valves may be automatically or manually opened and closed. For example, in certain embodiments, a clinician may present the device to a patient with the breath sensing channel valve 5 opened and the breath condensate sensing channel valve 6 closed, and instruct the patient to exhale into the input channel. The clinician may then close the valve 5 and open valve 6 and instruct the patient to exhale again to collect the breath condensate. In other embodiments, the valve timing is automated, either set by the clinician, or based on automatic determinations of when enough sample has been collected for a particular measurement. As discussed further below, in certain embodiments, the device automatically controls valves based on the breath cycle. In alternate embodiments, both valves may be opened during a combined breath/breath condensate measurement, with flow split into both channels 13 and 14. A valve may be closed if the breath or breath condensate measurement is not being performed. In alternate embodiments, the unit does not include one or more of valves 5 and 6.

If present, valves 5 and 6 may be any type of appropriate valve to regulate relatively low flow rate gas flow, including gate valves, diaphragm valves and the like. In many embodiments, valves 5 and 6 are one-way or check valves. Valves may be placed anywhere appropriate. In the example shown, breath gas sample channel 13 includes three sub-systems 3', 3" and 3'" and breath condensate gas sample channel 14 includes three sub-systems 4', 4" and 4'". A sample channel may contain any number of sub-systems, typically containing at least one subsystem for detection of one or more known or unknown analytes. Additional subsystem may be present as desired. A subsystem may include various features mounted to or within the channel's walls, or may include additional flow channels, a removable cartridge with inlet and outlet ports to connect to channel 13 or 14, a fixed housing with inlet and outlet ports to connected to channel 13 or 14 etc. The exact placement and configuration of the subsystems may vary depending on the system implementation.

Turning to FIG. 2, a flow path configuration including direct condensation on a sensor 34 is described. Breath gas flow channel 13 includes inline sub-systems 23 and 33: fluid conditioner sub-system 23 and gas phase in line detector 33. Breath condensate channel 14 includes a sub-system 34 for breath condensate detection. In the depicted embodiments, the gas sample entering channel 14 condenses directly on the breath condensate sensor 34. In certain embodiments in which direct condensation on the sensor surface is employed, the breath condensate channel may include a sub-system upstream of sensor 34 to prevent premature condensation on the channel walls.

Figure 3A:
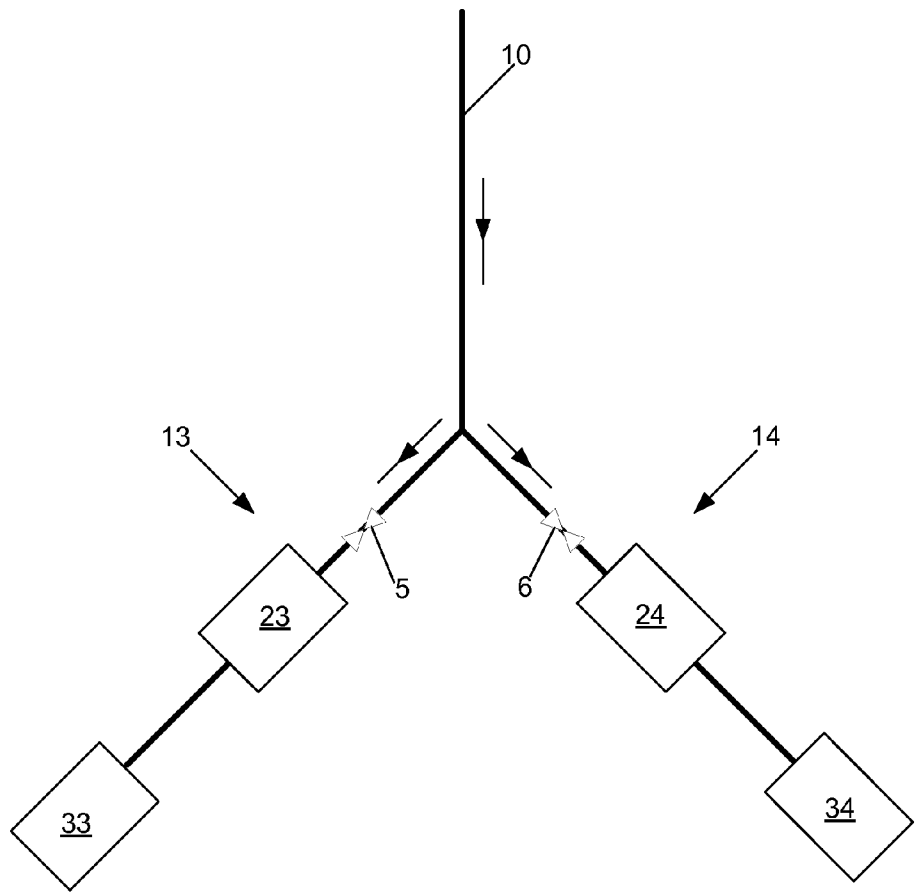
Figure 3B:
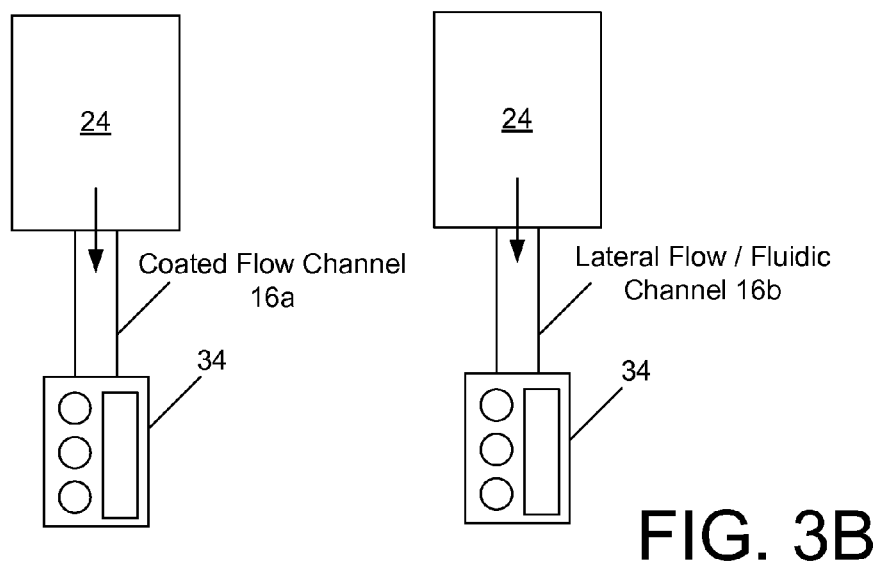

FIG. 3A presents a flow path configuration including a condensation subsystem upstream of the breath condensate sensor. Breath condensate sample channel includes condenser 24 and in line sensor 34. FIG. 3B shows examples of a portion of breath condensate flow channel 14, including condenser 24 and in line sensor 34. Condenser 24 and in line sensor 34 are connected via a liquid flow channel. As shown, two examples are presented: flow channel 16a is coated with electrolytes and/or other assay reagents, which are absorbed by the sample condensate as it travels through the channel; flow channel 16b is a lateral flow/fluidic channel. The channel may be a capillary flow channel or a microfluidic flow channel with or without microfluidic pumps. Further details of fluid flow from the condenser to the breath condensate sensor are given below.

Figure 4A:
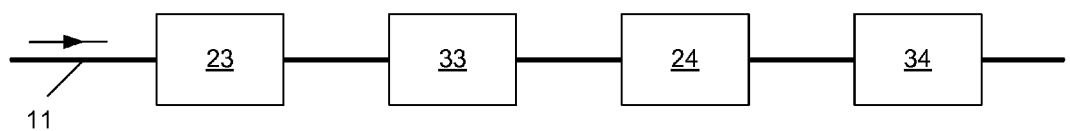
Figure 4B:
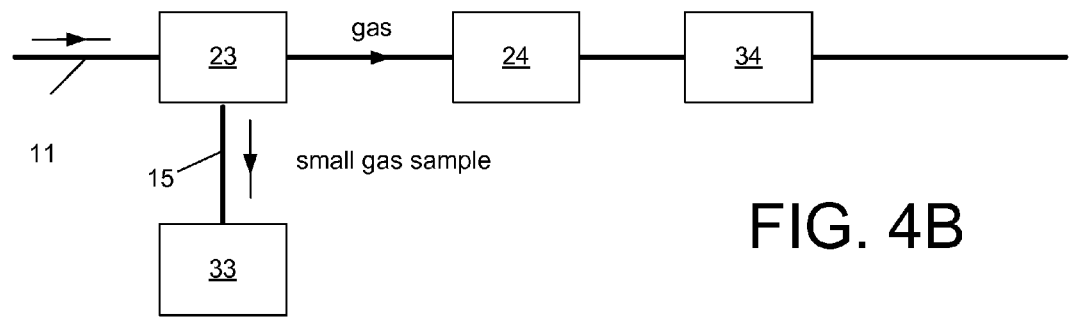
Figure 4C:
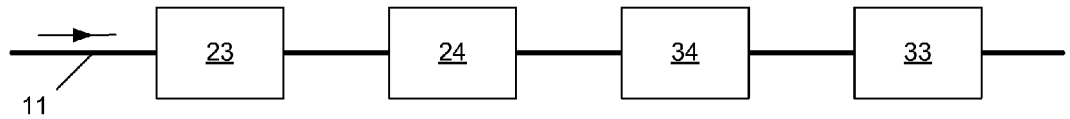
Figure 4D:
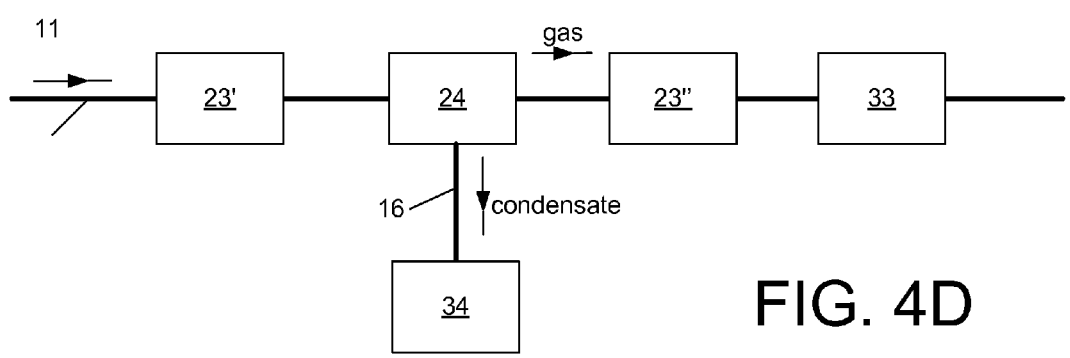

FIGS. 4A-4D provide examples of various implementations of serially arranged flow path configurations. First, in FIG. 4A, four sub-systems are depicted along a channel 11: gas conditioner 23, gas sensor 33, condenser 24 and condensate detector 34. A patient breaths into the unit, with the exhaled breath entering channel 11 directly or indirectly. The sample encounters gas conditioner and gas sensor 33, which measures the presence and/or quantity of a gas-phase analyte such as NO. All or a portion of the sample then passes to condenser 24. The condensate then continues to condensate sensor 34. According to various embodiments, the gas phase sample remaining after passing condenser 24 is diverted to an outlet channel (not shown) or a gas phase collection component (not shown) or is allowed to pass over condensate sensor as well. FIG. 4B depicts an arrangement in which the gas enters sub-system 23, which may measure and meter out a small gas sample 15 to gas sensor 33. For example, sub-system 23 may operate to collect at volume of gas from a particular part of the breath, e.g., based on the sampling time. The remainder of the gas continues to condenser 24 and condensate sensor 34. FIGS. 4C and 4D show examples of flow path configurations in which the condensate sub-systems are upstream of the gas-phase sub-systems. In FIG. 4B, the breath enters condenser 24, then condensate sensor 34, with the sample continuing onto gas phase conditioner 23 and gas phase sensor 24. Another example is depicted in FIG. 4C in which the sample encounters condenser 24. The condensate formed in condenser 24 is then directed to sample condenser 34 via channel 16, with the uncondensed gas continuing along channel 11 to encounter gas conditioner 23" and gas phase sensor 33.

As with all flow path configurations, the location and presence of particular sub-systems will vary according to the implementation. For example, in either of the examples depicted in FIGS. 4C and 4C, the gas sample may be treated as described above with respect to FIG. 4B. In another example, there may be multiple gas phase conditioners. An example is depicted in FIG. 4D with gas phase conditioner 23' upstream of condenser 24. Such a configuration may be employed, for example, to prevent any sample from condensing prior to reaching condenser 24. As described above, additional sub-systems may be present and/or certain sub-systems may not be present according to various embodiments. Generally, a combined breath/breath condensate unit includes at least a gaseous breath sample sensor, a condenser and a condensate sensor, with the condenser and condensate sensor combined into one sub-system in certain embodiments. Generally a breath condensate unit includes a condenser and a condensate sensor, with the condenser and condensate sensor combined into one sub-system in certain embodiments. As discussed, below, in certain embodiments, units may be modified from measurement to measurement in certain embodiments, with various sub-systems housed in removable single or multi-use cartridges.

Control of Sample Condensation

As described above, sample conditioning sub-systems may be located upstream of the sensor to manipulate the breath sample to specifically condense or specifically not condense. Moreover, within any subsystem (sensor, etc.), the breath sample may be manipulated to specifically condense or specifically not condense. Additional techniques may be employed to increase or decrease the amount of water vapor present within the subsystem and/or entire breath condensate sample channel and/or entire breath sample channel or portions thereof.

Sample condensation occurs when the gas temperature approaches and/or falls below the dew point of the gas. The dew point is a function of the amount of water vapor in the gas. The dew point is also influenced by constituents within the water vapor, for example salts. The occurrence of condensation below, at, or above the dew point also depends on the availability of nucleation sites for the water vapor to condense. The availability of nucleation sites promotes condensation, thus allowing for condensation to occur at a higher temperature than without nucleation sites. The gas may be condensed onto a variety of surfaces. These surfaces may be within a removable collection vessel facilitating off-line analysis. The surfaces may also be a sensor itself, such that the condensate forms directly on the sensor. High surface area and high thermal conductivity of CNTs facilitate condensation. The surface may also be attached to a fluid conduit, thus allowing the vapor to condense and then flow into a fluid channel. The fluid channel could be part of a microfluidic system, where the fluid is processed and analyzed.

In certain embodiments, the sample is condensed directly on the sensor and/or sensing element(s). Any type of sensor may be used including, electrochemical sensors, metal-oxide sensors, carbon nanotube-based sensors (FET, electrochemical, etc.) and optical sensors. The sensor can be of any type, multiples of a single type or combinations of several types.

In certain embodiments, in addition to the analyte sensing element, an additional sensor may be used for sensing the presence of the condensate, regardless of composition. This sensor could be used to determine if enough sample has condensed before starting the condensate-analysis. Any method can be used to detect the presence of condensate on the sensor element, for example but not limited to, conductance, capacitance, 4-wire conductivity, optical transmission and/or interference.

In the case of an electrical measurement, the electrodes for measurement can be placed on opposite end of the analyte-sensor element. In certain cases, the condensate-analysis sensor electrodes can also be used to sense for liquid presence. To condense, the sensor is maintained at a lower temperature by local cooling using a Peltier or other thermoelectric device, a cooling plate with manifolds, or by keeping the sensor cartridge in a refrigerator or freezer before use. The condensation will be caused by the temperature difference between the sensor and the exhaled patient breath.

The cooling element can be positioned in any appropriate position or configuration to allow the breath sample to condense directly on the sensor. For example, the condensate sensor element can be placed directly on top of a Peltier element. In certain embodiments, the sample breath is heated and/or humidified (increase RH) to cause condensation over the sensor/multiplex device. This may be in addition to or instead of cooling the sensor surface. A dew point calculation is performed to determine the exact conditions.

In an alternative embodiment, a condensation surface may be disposed in particular location and/or have a particular geometry that directs or transmits the condensate sample to the sensor. In an example, a condensation surface is disposed above the sensor surface: condensate forms on the condensation surface and is then directed to the sensor surface by gravity and/or other forces. The condensation surface may be a particular geometry that facilitates the transmission.

In certain embodiments, timers are incorporated into the devices. For example, in a device containing multiple sensors, each sensor may be activated to condense and sense at a specific time. In this manner, readings every hour, etc. may be taken. Sensing protocols are programmed, with heating and cooling controlled to allow or prevent condensation on a particular sensor as needed. In certain embodiments, sensing may be programmed to coordinate with external events (e.g., morphine injection).

In certain embodiments, a separate chamber along the flow path is used to collect the condensed sample, e.g., as depicted schematically in FIG. 3B. The condensed sample is transported to the sensor through a fluidic channel/lateral flow path. The channel may have a coating of electrolytes for electrochemical detection that are dissolved in the sample as it is transported. Transportation between the condenser and the sensor is discussed in more detailed below. As with condensing directly on the sensor, a conductivity measurement may be carried out to normalize the sensor response. The amount of condensate per breath and how many breaths are required to gather required amount of fluid is determined to obtain the analyte concentration detectible by the sensor and is clinically relevant.

According to various embodiments, a cooling plate or device is located below the sensor (or other location where condensation is desired). This may be a thermoelectric cooler, a plate with cooling channels, etc. A cooler may be fabricated in a wafer (e.g., to provide a two layer wafer with cooling and sensor) or attached to the bottom of a sensor device. In certain embodiments, cooling is highly localized to the sensor to prevent condensation elsewhere. In certain embodiments, cooling temperature is regulated, e.g., for biochemical applications.

A condenser sub-system and/or a detector sub-system including a condenser, includes a condensation surface. In certain embodiments the condensation surface is a material having a high thermal conductivity and/or high surface area. In certain embodiments, the condensation surface is a mesh material through which the gas samples passes, with condensate forming on the mesh. In certain embodiments, the condensate is a metal wire mesh. The mesh material may be a planar wire mesh, with the sample flow perpendicular to the plane of the wire mesh, or it may be a three-dimensional wire mesh material through which the sample flows. The mesh structure may be of any configuration, such as criss-crossing wires at 90 degrees or any other angle. The mesh structure can also be formed by sets of parallel wires. The mesh orientation can be configured so as to optimize the flow of condensate on the mesh surface into a receiving section. Multiple planar wire meshes may be used in series to achieve a desired total surface area. Alternatively multiple parallel wires may form the condensing surface.

In certain embodiments, a single breath sample can provide sufficient breath condensate to assay its components and/or parameters, such as pH, conductivity, proteins, nucleic acids, metabolites, enzymes, etc. Based on the saturated vapor pressure of water, a typical 500 mL breath exhalation contains between 14 microliters (assuming 30° C. and 90% RH) and 20 microliters (assuming 35° C. and 100% RH). However, observed condensate recovery is less than 100%. According to various embodiments previously demonstrated, between about 1 microliter and 10 microliters condensate per breath is collected. In certain embodiments, 1 to 10 microliters is sufficient to assay the components and/or parameters of breath condensate, such as pH, conductivity, proteins, nucleic acids, metabolites, enzymes, etc. The high collect efficiency required to measure the condensate from a single breath is enabled by our novel designs.

In certain embodiments, it is advantageous to perform breath condensate assays on a breath-to-breath basis. The high surface area mesh condensing surfaces and low condensate volumes provide for the ability to perform breath condensate assays on a breath-to-breath basis. Furthermore, uniform condenser efficiency allows these measurements to be reproducibility and consistent over the breath cycle.

Also in certain embodiments, a gas sample may be prevented from condensing at one or more positions. Preventing condensation may be needed, e.g., due to environmental conditions and/or the proximity of a condenser. Preventing condensation, e.g., in a gas-conditioning subsystem, may involve heating the channel.

Condensate Transport

In certain embodiments, the devices described herein are configured to transport breath condensate from one or more condensation surfaces to one or more breath condensate sensors. In certain embodiments, one or more capillary flow channels are provided between a condensation surface and a sensor. In certain embodiments, a wicking membrane or other material is provided between a condensation surface and a sensor. In certain embodiments, one or more non-capillary flow channels are provided. In these embodiments, the fluid may be transported via one or more of the following forces: gravity, electrokinetic, pneumatic pressure, fluid pressure, vacuum, thermal, osmotic, pumping, bimetallic disc membranes, plungers. In certain embodiments, the patient's exhaled breath provides motive force for the condensate.

Figure 5:
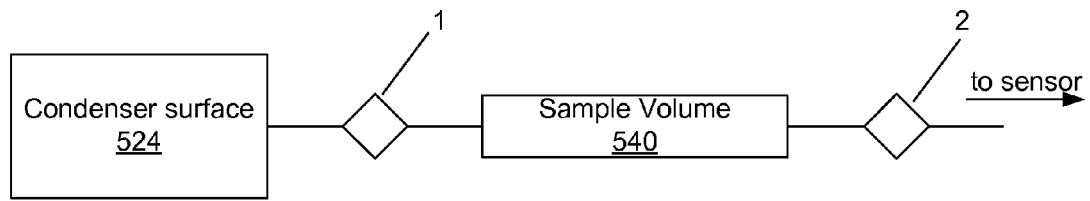
FIG. 5 is a schematic diagram of a portion of a flow path configuration for a breath condensate sampler and detector according to certain embodiments.

In certain embodiments, a metered amount of condensate is delivered from the condensate surface(s) to the sensor(s). In certain embodiments, the flow path from the condensate surface to the breath condensate sensors includes two valves defining a metered sample volume. FIG. 5 shows a block diagram of a portion of an exhaled breath condensate fluid path including condensation surface 524, sample volume 540 and first valve 1 and second valve 2. Sample volume 540 is of a defined size, e.g., 5 uL or 10 uL. As or after breath condenses on condensation surface 524, it moves into sample volume 540. Sample volume 540 may be a length of a longer microfluidic channel or may be a chamber along such a channel. Valve 2 is closed, allowing the condensate to collect in sample volume 540. Valve 1 remains open until sample volume 540 is filled, at which point it closes, trapping a precise amount of liquid within sample volume 540. Valve 2 may then be opened so that the precisely metered volume of condensate is moved toward the detector.

Gas-Phase Sensing

The breath sample gas may be passed by, through, across or adjacent to a gas-phase sensor element. The sensor can be of any type, multiples of a single type, combinations of several types, or any other variations, i.e. electrochemical, metal-oxide, carbon-nanotube, optical, field effect transistors. In certain embodiments, a desiccant may be used to remove water vapor from the breath as required. Additional scrubbers, catalytic converters, or other gas conditioning elements may be used according to various embodiments.

In certain embodiments, it is a specific gas volume from a particular phase of the respiratory cycle is analyzed. For example, in the case of NO monitoring, the clinically relevant region of the breath is analyzed. In one embodiment, valves as described above with respect to FIG. 1 are used to make sure that the gas-phase detection takes place first; an electronic reader is prompted to close the gas sample channel valve. Alternatively, the gas-phase and condensate-phase can occur serially. In other embodiments, the condensate-phase detection takes place prior to the gas-phase detection, using valves and/or serial arrangement of the detectors.

Gas-phase detectors may detect any gas-phase constituent of an exhaled breath sample. These include carbon dioxide, oxygen, nitric oxide, nitrogen, nitrogen dioxide, hydrogen peroxide, acetone, ammonia, sulfur compounds, acetylene, carbon monoxide, ethane and pentane. As indicated above, in certain embodiments, sensors having nanostructured sensing elements are provided. Examples of carbon nanotube (CNT) detector systems for nitric oxide, carbon dioxide and other breath constituents are described in the following publications, each of which is incorporated by reference herein: US Patent Publication No. 2007-0048180, titled "Nanoelectronic Breath Analyzer And Asthma Monitor," U.S. Patent Publication No. 2007-0048181, titled "Carbon Dioxide Nanosensor, And Respiratory CO2 Monitors," WO 2008-039165, also titled "Carbon Dioxide Nanosensor, And Respiratory CO2 Monitors," U.S. Patent Publication No. 2008-0221806, titled "Sensor Having A Thin-Film Inhibition Layer, Nitric Oxide Converter And Monitor," and U.S. Pat. No. 7,547,931, titled "Nanoelectronic Capnometer Adapter Including A Nanoelectronic Sensor Selectively Sensitive To At Least One Gaseous Constituent Of Exhaled Breath."

Breath Condensate Sensing

In certain embodiments, a breath condensate sampler and detector that enables real-time or near real-time detection and analysis is provided. According to various embodiments, this sampler may be combined with a breath (gas) sampler as described above. The breath condensate sampler may be employed with FET and/or electrochemical sensing devices and/or optical sensing devices. As described above, in certain embodiments, the sample is condensed directly on the sensor. This prevents waste and eliminates the necessity of fluid movement. A monitor, as described above, may be employed to sense whether there is enough condensate-liquid on the sensor prior to sensing. Contact electrodes on either end of the sensor enable detection of continuous film of liquid across the sensor element. In certain embodiments, contact electrodes are used to determine concentration or dilution of the exhaled breath condensate. For example, dilution of breath condensate by atmospheric water vapor may be determined by comparing a conductivity measurement to a baseline conductivity of condensate of atmospheric air. In certain embodiments, the sensor has multiple sensing electrodes to sense different analytes. In certain embodiments, a single device contains multiple sensors.

In certain embodiments, timers are incorporated into the devices. For example, in a device containing multiple sensors, each sensor may be activated to condense and sense at a specific time. In this manner, readings every hour, etc. may be taken. Sensing protocols are programmed, with heating and cooling controlled to allow or prevent condensation on a particular sensor, as needed. In certain embodiments, sensing may be programmed to coordinate with external events (e.g., morphine injection).

In certain embodiments, the sensor includes nanostructured elements, e.g., CNT-FETs, nanostructured electrochemical sensors. Because these sensors are small and require only a small amount of analyte, cooling requirements are low. For example, in certain embodiments, no more than a few microliters of breath condensate are required. In addition, because the time to obtain such a sample is low (e.g., one or a few exhalations), a clinician may be present to collect the sample. In other embodiments, optical sensors and other sensors may be used.

In certain embodiments, the amount of condensate on the sensor is controlled. According to various embodiments, this is done by condensing a controlled amount directly on the sensor or heating the sensor to drive excess condensate off the sensor, cooling from the bottom of a metered volume such as a well with electrodes or other monitor placed at the top of the well to sense when the well is full, etc. If necessary, lateral flow or microfluidic channels direct the metered volume to the sensor.

Breath condensate sensors may be used to detect any analyte present in exhaled breath and soluble in water. These include proteins and DNA. In a particular example, the sensors detect one or more cysteinyl leukotrienes (CysLTs), including LTC4, LTD4, and $LTE_4$. In a particular example, LTE4 is detected.

In certain examples, electrochemical sensors having nanostructured elements are used. These sensors require a small amount of analyte. As a result, the number of exhalations required is small, with a relatively short condensation time. This means that the condensation efficiency is uniform over the sample period. Electrochemical sensors for biochemical detection having CNTs and other nanostructured elements are described in U.S. Patent Publication No. 2008-0185295 incorporated by reference herein.

The use of CNTs for electrochemical measurements of various protein targets using electrochemical ELISA is described in the above-identified reference. In one example, CNTs are used for the detection of LTE4 combined with the sampling scheme described herein provides various options for the sensor configuration. For example, in a competitive assay for leuktrines, according to various embodiments, enzyme labels such as acetyl cholinesterase (AChE), horseradish peroxidase (HRP) etc. may be used as needed by the sample matrix, desired sensitivity and other assay requirements.

In certain applications it is advantageous to assay both the exhaled breath gas and exhaled breath condensate. In certain applications more accurate medical diagnostics can be achieved by obtaining information about both the exhaled breath gas and exhaled breath condensate.

In one application NO and LTE4 are measured using the combined breath and breath condensate sampler and detector units. The same methods may be applied to other analytes of interest in breath and breath condensate. Examples of targets in breath are acetone, ethane, hydrogen sulfide, oxygen, pentane, carbon disulfide. Examples of targets in breath condensate are glutathione, hydrogen peroxide, acetylcholine, and l-tyrosine. Markers for conditions like tuberculosis are also potential targets, for example bacteria and volatile organic compounds may be measured. In other embodiments, the measurement of $CO_2$ using CNT-FET based sensors and pH measurement by potentiometric method as a means of normalization of sensor response or as a diagnostic tool are other targets that are measured by the detector and condenser described herein. It is clear that the condenser and the detector are applicable for any condition where it is necessary to measure markers in breath and/or breath condensate.

In one application sensing of compounds such as acetone in breath using electrochemical enzymatic assay is accomplished. Enzymes such as secondary alcohol dehydrogenase combined with a nicotinamide adenine dinucleotide (NADH) cofactor producing hydrogen peroxide are used. In such applications it is very important to have enough enzyme on a small sensor. Small sensor design enables multiplexing with low volume of fluid. In such applications, nano structured materials such as carbon nanotubes offer the advantage of high surface area and biomolecule affinity that facilitates enzyme immobilization.

According to various embodiments, an exhaled breath condensate assay flow path configuration may include on or more of the following attributes, either alone or in any combination thereof: the flow channels may be coated with patches of sol gel containing fluorophore/indicator dye for contactless oxygen and pH measurement. Contactless conductivity measurement may be performed electrically using a pair of electrodes across a microfludic channel. Conductivity measurement may be used to ascertain the presence of certain volume of condensate on the electrodes. This is used as a feedback to a control valve. Oxygen, pH, conductivity and other measurements are used to normalize the analyte response.

In certain embodiments, a reporter antibody may be functionalized with an enzyme label, which may be coated inside the channels. The condensed liquid containing analyte will dissolve the reporter antibody and the analyte+reporter structure will bind with the capture antibody on electrode of an electrochemical sensor. In certain embodiments, carbon nanotube (CNT)-based electrochemical sensors are used. In order to take advantage of the increased stability of biomolecules after attachment to CNTs, the reporter antibodies may be immobilized on CNTs. CNTs can also be used to attach multiple enzyme labels per reporter antibody if improvement in sensitivity is realized by this approach. The improved reporter stability enabled by CNTs allows the device to be used in broad temperature range because the capture antibodies are already immobilized on the electrode with CNTs.

Cartridges

Figure 6A:
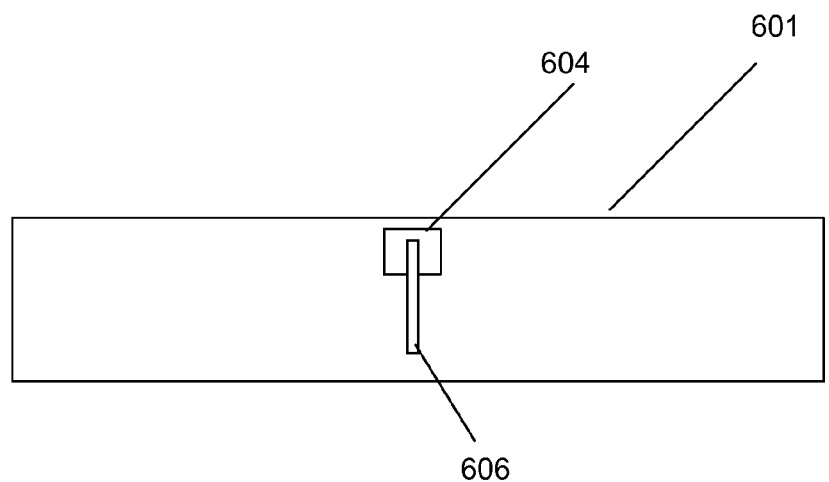
FIG. 6A is a schematic representation of a unit including breath condensate cartridge receiving area and active cooling mechanism according to certain embodiments.

In certain embodiments, one or more of the sub-systems is provided in a removable single or multi-use cartridge that is engageable with a larger unit. For example, one or more of the following is provided in a cartridge: gas-phase sensor, breath condensate sensor, condenser and/or condensation surface. In a particular embodiment, a cartridge is including a condensation surface, one or more condensate sensors and one or more channels to direct the condensate from the condensation surface to the sensor. FIG. 6A shows an exemplary embodiment of a breath/breath condensate unit 601 including cartridge slot 603 into which a single use cartridge fits into. The unit may also be a breath condensate only unit. A cooling mechanism 604 is configured to cool the condensation surface of the cartridge. The cooling mechanism may be a thermoelectric device, cooling channels, etc.

Figure 6B:
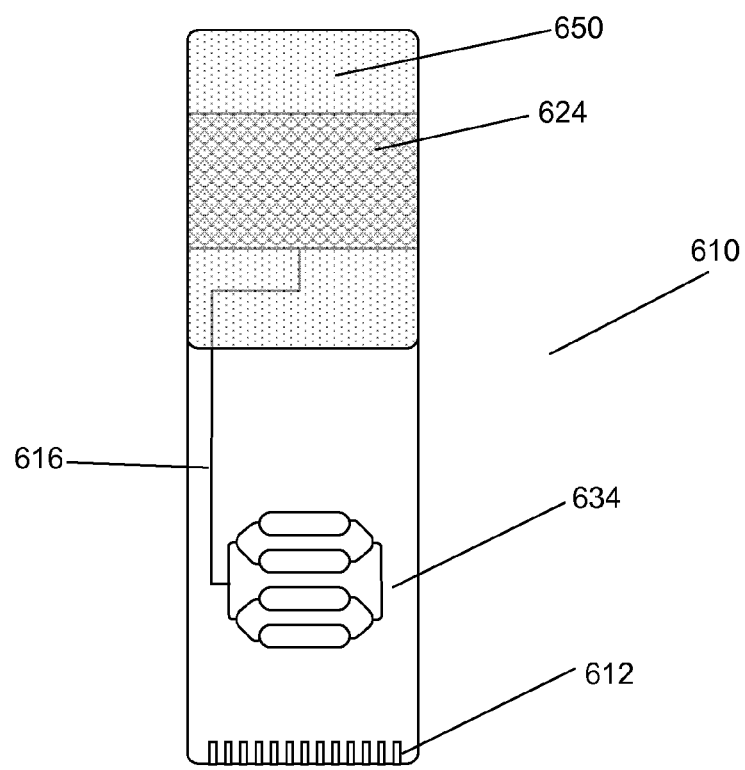
FIG. 6B depicts a single use condensate collector and detector cartridge that may be used in accordance with certain embodiments according to certain embodiments.

FIG. 6B shows an exemplary embodiment of a single use cartridge 610 engageable with a unit as depicted in FIG. 6A, including wire mesh condensation surface 624, breath condensate sensors 634 and fluid channel 616. Air sample flow is perpendicular to the plane of the wire mesh 624, in the direction into the page. The cartridge 610 is configured to engage with the unit 601 in slot 606. In the depicted embodiment, wire mesh 624 is surrounded by a thermally conductive surface 650 (e.g., a metal) that contacts the cooling mechanism 604. Electrical signals from sensors 634 are sent to contacts 612, which interface with electrical connections (not shown) in unit 601 to be sent for signal analysis.

Single-use cartridges may be used to prevent measurement-to-measurement sample contamination on the condensation surface and/or detector. In certain embodiments, a condensation surface is provided in the unit or in a separate cartridge from the detector and may be re-used after washing. In certain embodiments, a gas phase detector is in its own removable cartridge configured to engage with the breath/breath condensate unit.

In certain embodiments in which a breath-only measurement is desired with a combined breath/breath condensate unit, the breath condensate cartridge may be replaced by a blank cartridge.

Example EBC Flow Path Configurations

Figure 7:
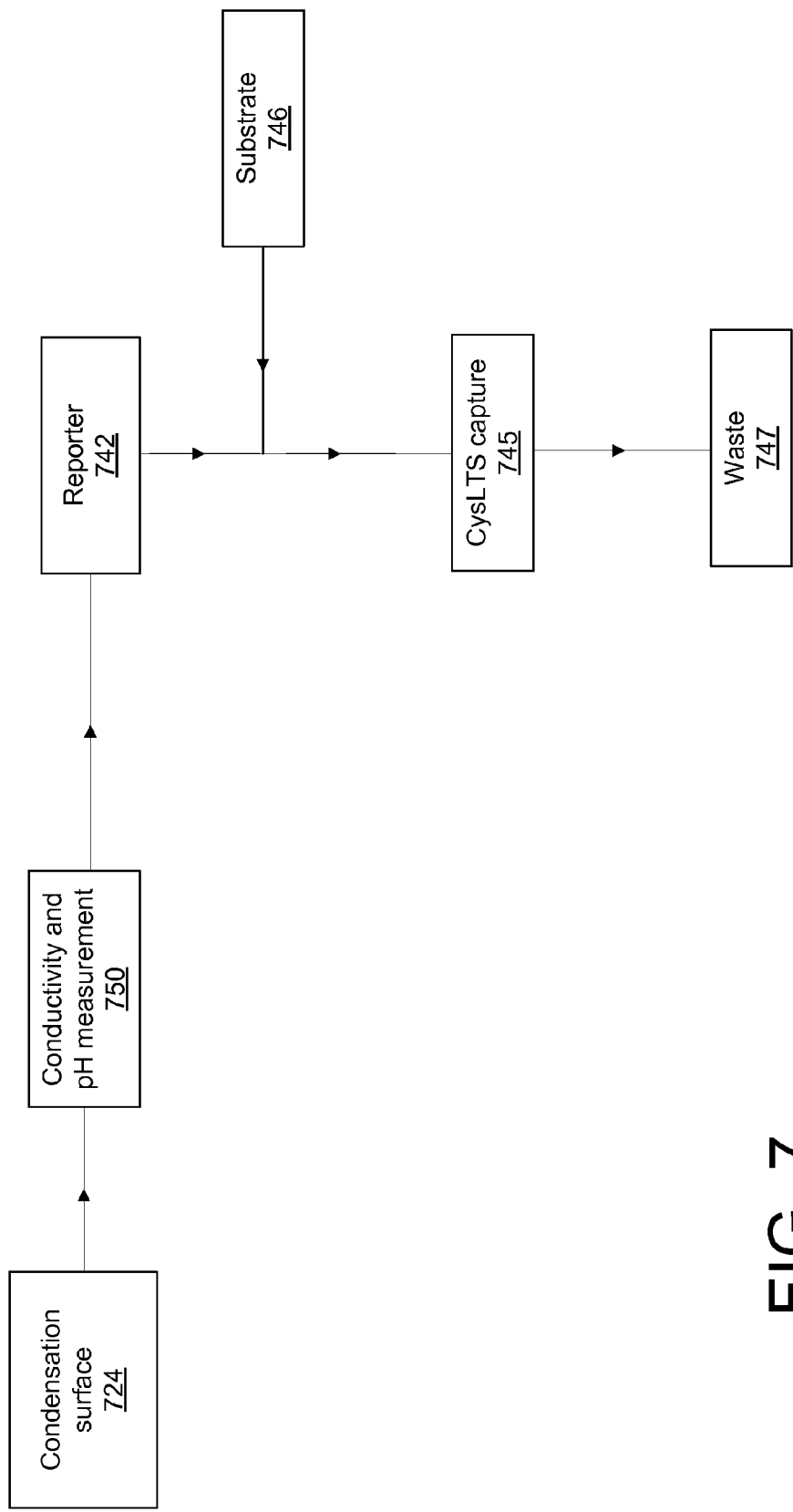
FIGS. 7 and 8 present schematic diagrams of flow path configurations for breath condensate samplers and detectors according to certain embodiments.

In certain embodiments, the breath condensate detectors are configured to perform real-time competitive or non-competitive breath condensate immunoassay. FIG. 7 shows an immunoassay flow path according to certain embodiments, including condensate containing analyte, capture species (if present) for the analyte, reporter and substrate. The depicted example flow path is for a leukotriene assay; however, one skilled in the art will understand how to modify the flow path appropriately for other analytes. The depicted flow path originates at the condensation surface 724. For example, the condensation surface is a wire mesh, or series of wire meshes on which condensate forms. From there the condensate travels toward a conductivity and pH measurement 750. As described below, conductivity may be used to detect condensate fill. The condensate then mixes with a reporter species 742, and condensate and reporter flow to interact with capture species 745. In the depicted example, the capture species is for a cysteinal leukotriene (CysLTs) for a leukotriene assay, however, any capture species may be used as appropriate. Substrate 746 is added to react with reporter. One of skill in the art will appreciate that the flow path configuration may also include other flows, e.g., washes. Example capture species for a leukotriene assay are antibodies, antibody fragments, molecular receptors, aptamers, oligonucleotides. Example reporter species for a leukotriene assay are enzymes, gold, latex, metal, etc. The reporter species can be linked to any type of recognition element, such as antibodies, antibody fragments (Fab, Fab2, Fc) aptamers, molecular receptors, oligonucleotides. Example wash substrates for a leukotriene assay are phosphate buffered solution. The wash solution may have detergents or surfactants added, such as Tween-20, SDS, Triton X100, NP40. Excess reporter and other waste is sent to waste 747.

Figure 8:
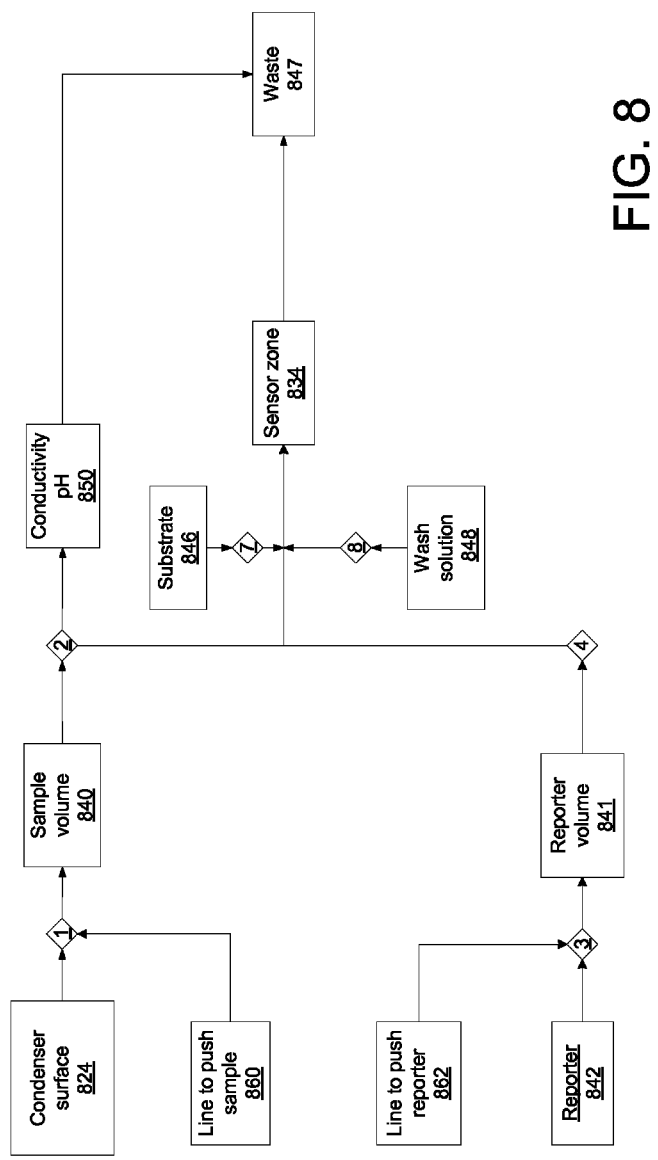

FIG. 8 shows a more detailed flow path configuration according to a specific embodiment. Here, condensate flows via capillary action or other means from condenser surface 824 to a sample volume 840 as described above with respect to FIG. 5. Fill of the sample volume channel or chamber 840 may be measured via conductivity/pH measurement area 850. Electrodes on either end of sample volume 840 provide an indication of when there is a conductive path through the sample volume 840, thereby indicating the sample volume 840 is full. Valves 1 and 2 are 3-way valves. Once the sample volume is full, the sample is pushed out of sample volume 840 using line 860 via valve 1. Line 860 may be a pneumatic or fluidic line. In embodiments wherein a cartridge is used, line 860 may be controlled off-cartridge by the main unit or controlled on-cartridge. Valve 2 is a three-way valve, allowing sample to reach conductivity measurement area 850 during the sample fill stage, then directing the sample toward the sensor zone 834 once fill is achieved. A reporter volume 841 similarly meters out a desired amount of reporter 842 via three-way valves 3 and 4 and line 862. Although not depicted, a reporter volume fill sensing mechanism may be present. Sample and reporter mix and flow to sensor zone 834, containing electrochemical sensors, or other types of liquid phase sensors as appropriate, and reagents as appropriate. Wash 848 and substrate 846 lines are controlled via one-way valves 8 and 7, respectively. Excess reporter, wash and other waste is sent to waste 847.

Figure 9:
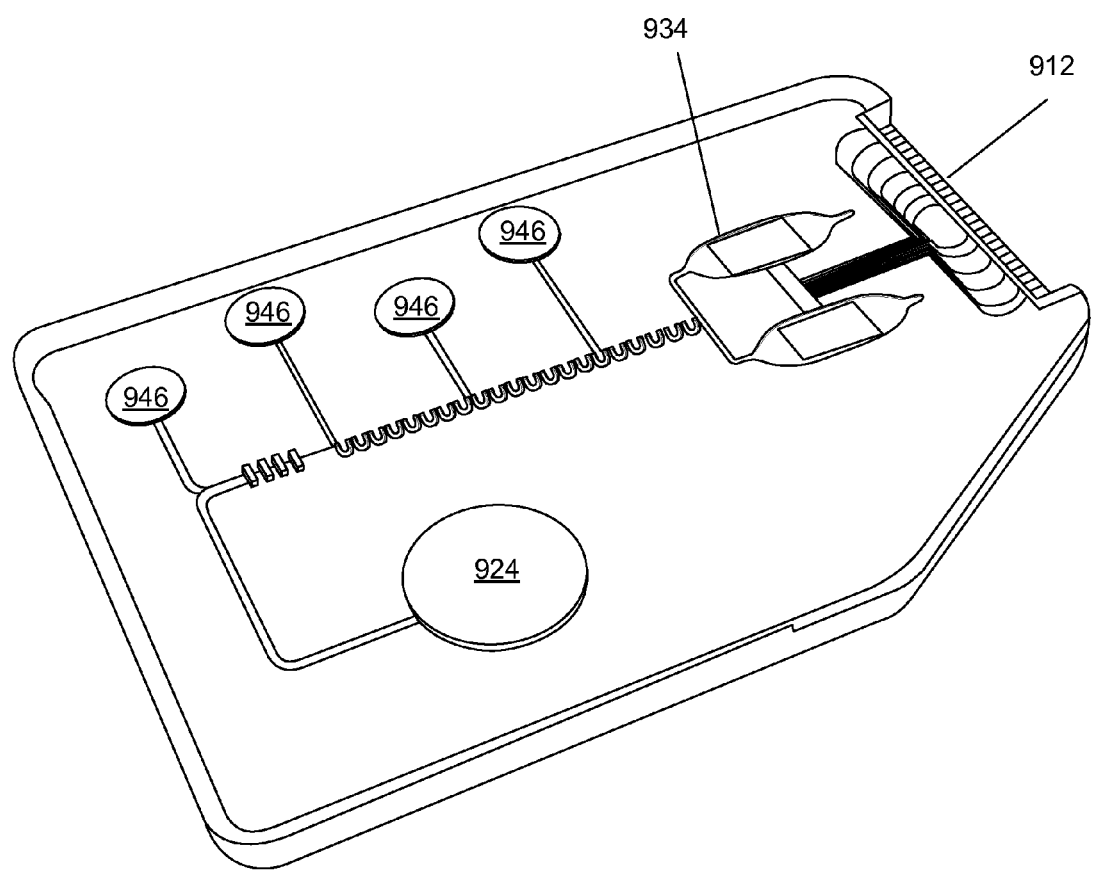
FIG. 9 a single use condensate collector and detector cartridge that may be used in accordance with certain embodiments according to certain embodiments.

The above-described breath condensate flow paths are implemented on a single or multi-use cartridge in certain embodiments. FIG. 9 provides an example of a single-use cartridge, including on-cartridge flow-through condensation surface 924, reagent/wash reservoirs 946, electrochemical sensors 934 and electrical contacts 912. Cooling for condensation surface 924 may be active or passive. In an active system, condensation surface 924 is surrounded by a heat sink (not shown), e.g., a thermoelectric cooler or cooling channels. Typically the cooling mechanism is off-cartridge, located in the main unit. In certain embodiments, a portion of the cartridge may be semiconductor material and may be part of a thermoelectric device. In a passive system, the cartridge is chilled prior to use.

As indicated above, in certain embodiments exhaled breath conductivity is used as a fill indicator. In certain embodiments, it may be used for condensate normalization. The conductivity is a measure of amount of water (dilution) in the sample. This information is used to adjust the sensor response for any dilution of the analyte. Conductivity may be measured by small interdigitated electrodes. In a cartridge format, a cartridge may include a layer including electrodes. An AC conductivity measurement is performed. As discussed above, the conductivity measurement may provide a signal to open one or more valves for further sample transport.

In certain embodiments, the pH of the exhaled breath condensate is measured. pH of the exhaled breath condensate has been shown to be a proxy measure of airway acidification. Airway acidification is prevalent in many respiratory diseases and conditions, including asthma, cystic fibrosis and chronic obstructive pulmonary disease (COPD). Typical ranges for EBC condensate are 7-8 for normative pH and <6 for acidification. As comparisons, pure water at 37° C. has a pH of 6.81 (slightly acidic due to self-ionization) and blood has a pH of 7.35-7.45.

The EBC pH measurement may be potentiometric or amperometric. In certain embodiments, the measurement is amperometric for ease of fabrication, requiring only an ion-selective membrane to be placed over electrodes. For both potentiometric and amperometric measurements, an ion-selective membrane is used to confer specificity to $H^+$ ions. One example ionophore H+ selective membrane material is TDDA.

Combined Unit

Figure 10A:
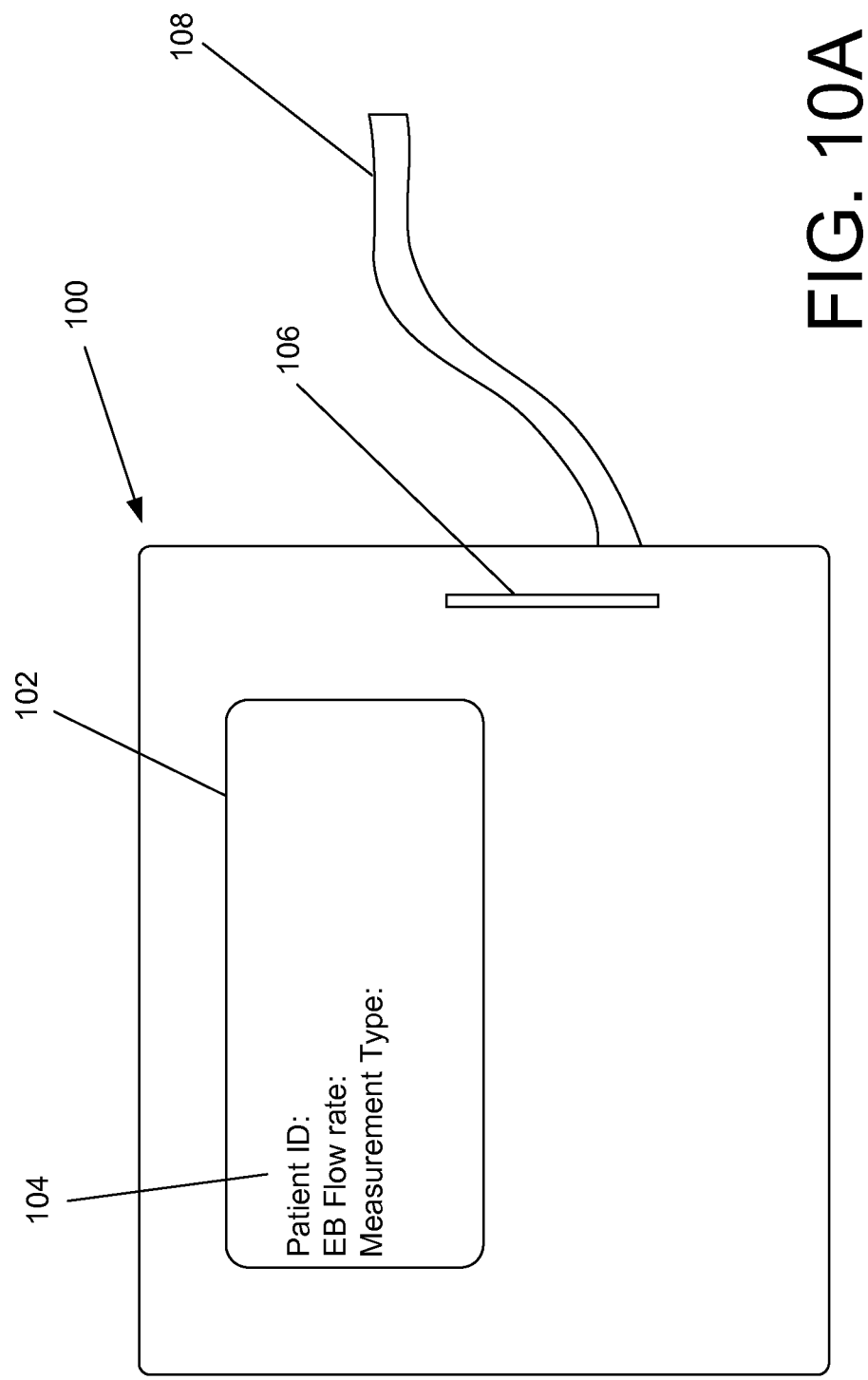
FIGS. 10A and 10B depict schematic diagrams of combined breath condensate and breath sampler and detector according to certain embodiments.
Figure 10B:
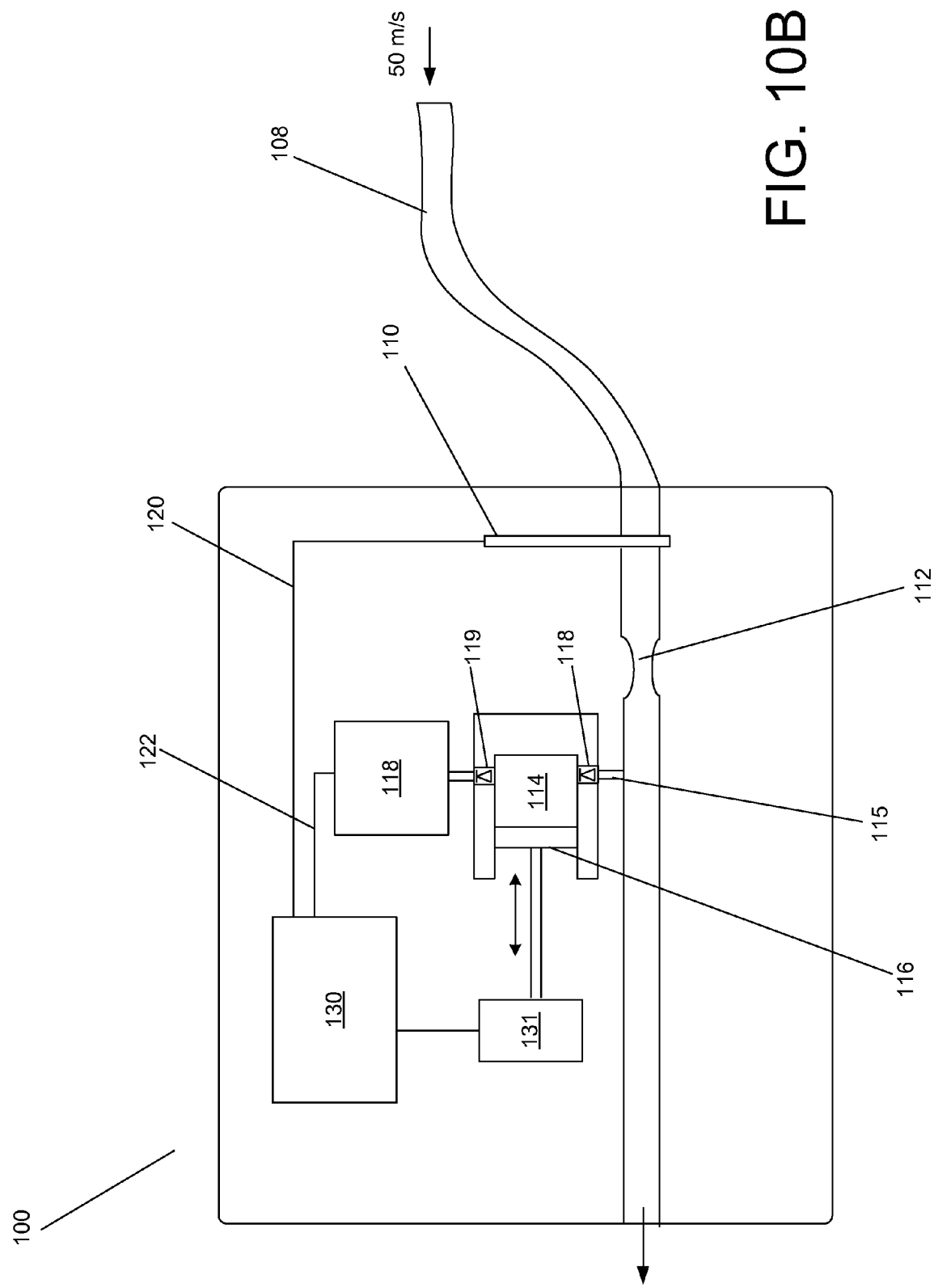

As described above, in certain embodiments, the sampling scheme provides breath condensate and breath measurements in a combined unit. FIGS. 10A and 10B provide a schematic representation of various components of such a unit 100 according to various embodiments. For clarity, certain components are not depicted. First, in FIG. 10A, an external front view of unit 100 is depicted. It includes a housing 101, typically a plastic material. Display 102 may be provided to display information 104 relevant to the measurement at hand. In certain embodiments, display 102 is a touchscreen input as well as output interface, accepting input relevant to the assay being conducted, patient, etc. In other embodiments, unit 100 includes a separate input interface (e.g., a keyboard) or is connected to an external input interface. Unit 100 includes a cartridge-accepting slot 106, as described above with reference to FIG. 6A. In use, a patient breathes into an adapter (not shown) in fluid communication with channel 108, which may be partially or wholly made of tubing or other material, FIG. 10B depicts schematically various internal components of the unit 100. Sample (e.g., 50 m/s) flows the unit 100 via channel 108. In the depicted embodiment, it flows through a flow through condenser in cartridge 110, which has been inserted into slot 106. If a breath condensate measurement is not desired, cartridge 110 may be a blank cartridge allowing flow through of the sample. Condensate forms and is directed to one or more sensor as described above with respect to FIGS. 7-9. In certain embodiments, about 5 microliters per breath is formed and directed to one or more sensors.

The sample (minus the small amount of now condensed water vapor) flows through the flow through condenser in channel 108. In certain embodiments an orifice 112 creates a small amount of back pressure. A flow meter is disposed to provide accurate readings of the exhaled breath flow rate. The flow is determined by measuring the pressure drop across the orfice. This is the low-cost method of measuring flow. If a flow-meter component was used, it could be installed between the patient and before the NO subsystem (since the NO subsystem pulls air from the main line and would thus alter flow measurements done after the NO subsystem). As breath is captured, the flow rate is validated. At 115, a predetermined amount of breath sample (e.g., 5 ml/s) enters a gas sample volume 114. Gas sample volume 114 is controlled by piston 116. Piston controller 131, e.g., a screw drive, pulls the piston to the left to create a vacuum in the defined volume, allowing sample to flow through valve 117. Once the sample volume is full, valve 117 closes. Valve 119 opens allowing the sample to flow to gas-phase detector 118.

In certain embodiments, the valves are controlled to allow sample to collect only at a specific point in the respiratory cycle according to protocols of the measurement. For example, valve 116 may be opened only after a pre-determined time after exhalation onset. Also in certain embodiments, validating exhaled breath flow rates includes opening a bypass valve such that a breath that falls outside a range of acceptable flow rates (for example, if a patient coughs) is not sent to a sensor.

Signals from EBC cartridge 110 and gas phase sensor 122 are sent to controller and data processing unit 130 via connections 120 and 122, respectively. In the depicted embodiment, controller and data processing unit 130 also controls various aspects of the sampler and detector unit, including piston controller 117, valves 117 and 119, valves on cartridge 110, display of information 104, etc. One of skill in the art will appreciated that one or more software and/or hardware components may be used for the control and data processing functions. In another embodiment, cartridge 110 and slot 106 are disposed such that the exhaled breath flows through the condenser after the gas phase sample is drawn into volume 114. In certain embodiments, two such cartridge-receiving slots may exist, one before the gas phase sampling and one after, allowing a clinician to choose and insert the appropriate cartridge depending on the particular measurement.

Although the foregoing invention has been described in some detail for purposes of clarity of understanding, it will be apparent that certain changes and modifications may be practiced within the scope of the appended claims. It should be noted that there are many alternative ways of implementing the processes, systems and apparatus of the present invention. Accordingly, the present embodiments are to be considered as illustrative and not restrictive, and the invention is not to be limited to the details given herein.

All references cited herein are incorporated by reference for all purposes.

The invention claimed is:

1. A portable unit for breath sampling and detecting comprising:
   a portable adapter configured to receive an exhaled breath sample from a patient;
   a channel in fluid communication with the adapter;
   a condenser disposed within the channel to condense water vapor in exhaled breath sample, said condenser comprising a condensation surface;
   a portable exhaled breath condensate sensor coupled to or integral with the adapter, configured to detect one or more analytes present in the condensed water vapor, wherein the condensation surface and the exhaled breath condensate sensor are contained in a removable cartridge;
   a flow channel disposed between the condensation surface and the exhaled breath condensate sensor; and
   a portable gas-phase detector coupled to or integral with the adapter, configured to detect one or more gas-phase analytes in the exhaled breath sample,
   wherein the portable adapter, portable exhaled breath condensate sensor and portable gas-phase detector together form the portable unit.

2. The portable unit of claim 1, wherein the exhaled breath condensate sensor is an electrochemical sensor.

3. The portable unit of claim 2, wherein the exhaled breath condensate sensor is an electrochemical sensor comprising a nanostructured sensing element.

4. The portable unit of claim 3, wherein the nanostructured sensing element is a carbon nanotube (CNT).

5. The portable unit of claim 1, wherein the condenser is configured for active cooling.

6. The portable unit of claim 1, wherein the condenser is configured for passive cooling.

7. The portable unit of claim 1, further comprising a thermoelectric device in thermal contact with the condensation surface.

8. The portable unit of claim 1, further comprising cooling channels in thermal contact with the condensation surface.

9. The portable unit of claim 1, wherein the condensation surface is a surface of the exhaled breath condensate sensor.

10. The portable unit of the any claim 1, wherein the condensation surface is a wire mesh.

11. The portable unit of claim 1, wherein the channel bifurcates into first and second sub-channels, the condenser in the first sub-channel and the gas phase detector disposed in the second sub-channel or a branch thereof.

12. The portable unit of claim 1, further comprising a capillary flow channel disposed between the condensation surface and the exhaled breath condensate sensor.

13. The portable unit of claim 1, further comprising a microfluidic flow channel disposed between the condensation surface and the exhaled breath condensate sensor.

14. The portable unit of claim 1, wherein the flow channel is coated with a reagent, and wherein the reagent comprises fluorophores or other indicator dyes provided in a sol gel coating the flow channel.

15. The portable unit of claim 1, further comprising a liquid-detecting sensor configured to detect whether sufficient condensed water vapor is present on the exhaled breath condensate sensor before the exhaled breath condensate sensor detects the one or more analytes present in the condensed water vapor.

16. The portable unit of claim 15, wherein the liquid-detecting sensor comprises contact electrodes on opposing sides of the exhaled breath condensate sensor, configured to help detect whether there is a continuous film of water vapor across the exhaled breath condensate sensor.

17. The portable unit of claim 1, further comprising a metered sample volume for holding the condensed water vapor before delivery to the exhaled breath condensate sensor, wherein the metered sample volume is configured to provide a specific and uniform volume of condensed water vapor to the exhaled breath condensate sensor.

18. The portable unit of claim 17, wherein the metered sample volume comprises a channel having a valve on each end.

19. A portable unit for breath sampling and detecting comprising:
   a portable adapter configured to receive an exhaled breath sample from a patient;
   a channel in fluid communication with the adapter;
   a condenser disposed within the channel to condense water vapor in exhaled breath sample, said condenser comprising a condensation surface;
   a portable exhaled breath condensate sensor coupled to or integral with the adapter, configured to detect one or more analytes present in the condensed water vapor;
   a flow channel disposed between the condensation surface and the exhaled breath condensate sensor;
   a portable gas-phase detector coupled to or integral with the adapter, configured to detect one or more gas-phase analytes in the exhaled breath sample; and
   timers that activate one or more of the exhaled breath condensate sensor and gas-phase detector at appropriate time(s),
   wherein the portable adapter, portable exhaled breath condensate sensor and portable gas-phase detector together form the portable unit.

20. The portable unit of claim 19, wherein the timers are configured to initiate periodic measurements over time.

21. The portable unit of claim 20, wherein the timers are additionally configured to cause the exhaled breath sample to be condensed or vaporized as needed for the periodic measurements.

22. The portable unit of claim 19, wherein the exhaled breath condensate sensor is an electrochemical sensor comprising a nanostructured sensing element.

23. The portable unit of claim 22, wherein the nanostructured sensing element is a carbon nanotube (CNT).

24. The portable unit of claim 19, wherein the condensation surface is a surface of the exhaled breath condensate sensor.

25. A portable unit for breath sampling and detecting comprising:
   a portable adapter configured to receive an exhaled breath sample from a patient;
   a channel in fluid communication with the adapter;

a condenser disposed within the channel to condense water vapor in exhaled breath sample, said condenser comprising a condensation surface;

a portable exhaled breath condensate sensor coupled to or integral with the adapter, configured to detect one or more analytes present in the condensed water vapor;

a flow channel disposed between the condensation surface and the exhaled breath condensate sensor;

a portable gas-phase detector coupled to or integral with the adapter, configured to detect one or more gas-phase analytes in the exhaled breath sample; and a metered sample volume for holding the condensed water vapor before delivery to the exhaled breath condensate sensor, wherein the metered sample volume comprises a well having a monitoring device that detects when the well is full of condensed water vapor, wherein the metered sample volume is configured to provide a specific and uniform volume of condensed water vapor to the exhaled breath condensate sensor, and wherein the portable adapter, portable exhaled breath condensate sensor and portable gas-phase detector together form the portable unit.

26. The portable unit of claim 25, wherein the exhaled breath condensate sensor is an electrochemical sensor comprising a nanostructured sensing element.

27. The portable unit of claim 26, wherein the nanostructured sensing element is a carbon nanotube (CNT).

28. The portable unit of claim 25, wherein the channel bifurcates into first and second sub-channels, the condenser in the first sub-channel and the gas phase detector disposed in the second sub-channel or a branch thereof.

29. A portable unit for breath sampling and detecting comprising:

a portable adapter configured to receive an exhaled breath sample from a patient;

a channel in fluid communication with the adapter;

a condenser comprising a condensation surface disposed within the channel for condensing water vapor in the exhaled breath sample;

a portable exhaled breath condensate sensor coupled to or integral with the adapter, configured to detect one or more analytes present in the condensed water vapor, wherein the condensation surface is a surface of the exhaled breath condensate sensor such that the exhaled breath sample condenses directly on and is analyzed on the condensation surface of the exhaled breath condensate sensor;

timers that activate one or more of the exhaled breath condensate sensor and gas-phase detector at appropriate time(s); and a portable gas-phase detector coupled to or integral with the adapter, configured to detect one or more gas-phase analytes in the exhaled breath sample, wherein the portable adapter, portable exhaled breath condensate sensor and portable gas-phase detector together form the portable unit.

30. The portable unit of claim 29, further comprising a liquid-detecting sensor configured to detect whether sufficient condensed water vapor is present on the exhaled breath condensate sensor before the exhaled breath condensate sensor detects the one or more analytes present in the condensed water vapor.

31. The portable unit of claim 30, wherein the liquid-detecting sensor comprises contact electrodes on opposing sides of the exhaled breath condensate sensor, configured to help detect whether there is a continuous film of water vapor across the exhaled breath condensate sensor.

32. The portable unit of claim 29, wherein the exhaled breath condensate sensor is an electrochemical sensor comprising a nanostructured sensing element.

33. The portable unit of claim 32, wherein the nanostructured sensing element is a carbon nanotube (CNT).

34. The portable unit of claim 29, wherein the channel bifurcates into first and second sub-channels, the condenser in the first sub-channel and the gas phase detector disposed in the second sub-channel or a branch thereof.

35. The portable unit of claim 29, wherein the timers are configured to initiate periodic measurements over time.

36. The portable unit of claim 35, wherein the timers are additionally configured to cause the exhaled breath sample to be condensed or vaporized as needed for the periodic measurements.

* * * * *